United States Patent
Luyendijk et al.

(10) Patent No.: US 6,472,354 B2
(45) Date of Patent: Oct. 29, 2002

(54) PROCESS FOR MANUFACTURING SULPHURIZED OLEFINS

(75) Inventors: Piet Luyendijk, Oostvoorne (NL); Jean-Francois Devaux, Jurancon (FR); Bernard Monguillon, Salies de Bearn (FR)

(73) Assignee: Atofina, Puteaux (FR)

( * ) Notice: Subject to any disclaimer, the term of this patent is extended or adjusted under 35 U.S.C. 154(b) by 0 days.

(21) Appl. No.: 09/841,241

(22) Filed: Apr. 25, 2001

(65) Prior Publication Data

US 2002/0016510 A1 Feb. 7, 2002

(30) Foreign Application Priority Data

Apr. 28, 2000 (FR) .............................................. 00 05498

(51) Int. Cl.[7] ..................... C10M 135/02; C07C 319/04
(52) U.S. Cl. ....................... 508/324; 508/201; 508/207; 568/18; 568/59; 568/72
(58) Field of Search .......................................... 508/324

(56) References Cited

U.S. PATENT DOCUMENTS

| | | | |
|---|---|---|---|
| 4,119,549 A | 10/1978 | Davis | 508/324 |
| 4,119,550 A | 10/1978 | Davis et al. | 508/324 |
| 4,147,640 A * | 4/1979 | Jayne et al. | 508/324 |
| 4,191,659 A | 3/1980 | Davis | 508/324 |
| 4,344,854 A * | 8/1982 | Davis et al. | 508/324 |
| 4,584,113 A | 4/1986 | Walsh | 508/331 |
| 4,661,274 A * | 4/1987 | Horodysky et al. | 508/324 |
| 5,091,112 A | 2/1992 | Perozzi et al. | 252/387 |
| 5,155,275 A | 10/1992 | Shaw | 568/21 |
| 5,174,922 A | 12/1992 | Perozzi et al. | 252/395 |
| 5,206,439 A | 4/1993 | Shaw | 568/21 |
| 5,208,382 A | 5/1993 | Perozzi et al. | 568/22 |
| 5,218,147 A | 6/1993 | Shaw | 568/21 |
| 5,242,613 A | 9/1993 | Ozbalik et al. | 508/324 |
| 5,338,468 A | 8/1994 | Arvizzigno et al. | 508/570 |
| 5,403,961 A | 4/1995 | Shaw | 568/21 |
| 5,457,234 A | 10/1995 | Shaw | 568/21 |
| 5,523,005 A * | 6/1996 | DiBiase et al. | 508/324 |
| 5,530,163 A | 6/1996 | Shaw | 568/26 |
| 5,559,271 A | 9/1996 | Shaw et al. | 568/21 |
| 5,726,253 A | 3/1998 | Le Perchec et al. | 525/359.1 |
| 5,767,229 A | 6/1998 | Arretz et al. | 528/374 |
| 5,786,511 A | 7/1998 | Arretz | 568/21 |
| 5,817,716 A | 10/1998 | Le Perchec et al. | 525/54.11 |

FOREIGN PATENT DOCUMENTS

| | | |
|---|---|---|
| EP | 0 076 376 | 4/1983 |
| EP | 0 342 454 A1 | 11/1989 |
| EP | 0 554 011 A2 | 8/1993 |
| EP | 0 714 970 A1 | 6/1996 |
| EP | 0 714 971 A1 | 6/1996 |
| EP | 0 201 197 A1 | 1/1999 |
| EP | 0 889 030 A1 | 1/1999 |
| EP | 0 931 789 A1 | 7/1999 |
| EP | 0 933 358 A1 | 8/1999 |
| FR | 2 607 496 | 6/1988 |
| FR | 2 630 104 | 10/1989 |
| FR | 2 757 534 | 6/1998 |
| JP | 58-140063 | 8/1983 |
| JP | 11-246518 | 9/1999 |
| WO | WO 92/00367 | 1/1992 |
| WO | WO 92/03524 | 3/1992 |
| WO | WO 97/24416 | 7/1997 |

\* cited by examiner

*Primary Examiner*—Ellen M. McAvoy
(74) *Attorney, Agent, or Firm*—Smith, Gambrell & Russell, LLP

(57) ABSTRACT

To manufacture sulphurated products derived from olefin(s) by sulphurization using sulphur and hydrogen sulphide, the reaction is carried out in the presence of a solid acid catalyst and of a solid basic catalyst.

24 Claims, No Drawings

PROCESS FOR MANUFACTURING SULPHURIZED OLEFINS

FIELD OF THE INVENTION

The present invention relates to the field of sulphurized olefins and more particularly its subject is a new process for preparing sulphurized olefins which are pale in color, by sulphurization using sulphur and hydrogen sulphide.

BACKGROUND OF THE INVENTION

Sulphurized olefins are products widely used for sulphurizing catalysts and as additives for lubricants or for elastomers. These products are essentially composed of mixtures of organic sulphides, disulphides and polysulphides.

The person skilled in the art knows of numerous processes for preparing sulphurized olefins or organic polysulphides. A first family of processes consists in reacting a mercaptan and sulphur in the presence of a basic catalyst. These processes, described in the patents FR 2 607 496 and FR 2 630 104, for example, are costly, since they require use of mercaptans, which themselves have to be produced from olefins or from alcohols.

The process described in the patent EP 342 454 for preparing dialkyl sulphides and dialkyl polysulphides from olefins is in fact a two-step process, in which initially an $H_2S$+olefin reaction takes place in the presence of a solid catalyst to form a mercaptan and, secondly, this mercaptan is brought into contact with sulphur and with another heterogeneous catalyst, to form a polysulphide. This process has the disadvantage of requiring two steps in succession (2 different reactors), with elevated temperatures.

Other processes which can give sulphurized olefins have been proposed:

1) The olefin+sulphur reaction in the absence of $H_2S$ generally prepares colored products. To avoid this disadvantage, operation in the presence of water, or washing with water, has been proposed, but this creates problems in separation of the aqueous phase and in disposing of the aqueous effluent. Processes of this type are described in the patents U.S. Pat. No. 5,338,468, WO 92/03524, WO 92/00367, WO 97/24416, EP 714 970, EP 714 971 and FR 2 757 534. In all these processes, elevated temperatures are required for good conduct of the reaction. The patent EP 201 197 describes the sulphur+olefin reaction at a temperature of 140 to 180° C.

2) The olefin+sulphur+$H_2S$ reaction has been described in the patents EP 554 011, EP 889 030, U.S. Pat. Nos. 4,119, 549, 4,119,550, 4,191,659 and 4,584,113 and the application JP 11-246518. However, elevated temperatures are required for good conduct of the reactions (usually above 110° C. to give significant conversion of the reactants) and/or the pressures mentioned are usually very high.

DESCRIPTION OF THE INVENTION

The new process now found for preparing sulphurized olefins by sulphurization using sulphur and $H_2S$ in the presence of solid catalysts provides clear, pale-colored products and has the advantage of requiring only slightly elevated temperatures, generally well below 110° C., and of permitting operations at only slightly elevated pressures. In addition, the use of solid catalysts allows very ready separation of the catalyst from the final product; using simple filtration it is possible to reuse the catalysts and to obtain a final product which is stable since it is free from catalysts. This process also allows the reaction to be realized in just one step.

The process according to the invention for preparing sulphurized olefins by sulphurization using sulphur and hydrogen sulphide is characterized in that the reaction is carried out in the presence of a solid acid catalyst and of a solid basic catalyst, in just one step.

There is a very wide range of suitable solid acid catalysts for use according to the invention, comprising, for example, various polymers and copolymers having acid functions and known in the art, such as cation-exchange resins, zeolites of acid character, silica-aluminas, sulphated zirconias or supported heteropolyanions, or a mixture of these.

Non-limiting mention may be made of sulphonated resins based on crosslinked polystyrene (preferably crosslinked with divinylbenzene), acrylic or phenylacrylic resins with free carboxyl groups, resins of phenol-formaldehyde type derived from phenolsulphonic acids, lignosulphonic exchangers, etc. . . . . . Resins of this type are available commercially with various names, in particular Amberlite, Dowex, Diaion, Duolite, Levatit, etc. Sulphonated copolymers of styrene with divinylbenzene are most particularly suitable. On the other hand, known copolymers of tetrafluoroethylene with a perfluorosulphonic acid, which have the name Nafion, can be employed advantageously. The solid acid resin is preferably used as dry as possible.

There is a very wide range of suitable solid basic catalysts for use according to the invention, comprising, for example, polymers or copolymers well known in the art and having basic functions, such as anion-exchange resins, zeolites of basic character, an alumina or silica-alumina doped with alkali metals or with alkaline earth metals, or a mixture of these catalysts.

Non-limiting mention may be made of resins based on crosslinked polystyrene, particularly crosslinked with divinylbenzene, acrylic or phenylacrylic resins, acrylic resins crosslinked with divinylbenzene, or resins of phenol-formaldehyde type. These resins bear primary, secondary or tertiary amine, quaternary ammonium, polyethylene polyamine, guanidine or amidine functional groups. Resins of this type are described in the patents FR 2 630 104, U.S. Pat. Nos. 5,786,511, 5,767,229, EP 931 789, U.S. Pat. Nos. 5,726,253 and 5,817,716, for example.

Anion-exchange resins which may be used are commercially available with a variety of names, such as Amberlite, Amberlyst, Diaion, Dowex, Duolite, Levatit, Reillex, etc.

In the case of the resins with quaternary ammonium functions, preconditioning prior to use could prove useful, for example treatment with sodium hydroxide followed by washing with water and drying.

The efficacy of the anion-exchange resins is generally improved if they are used as dry as possible.

The zeolites of basic character which may be used according to the invention are aluminosilicates characterized by a well-defined pore size and a large specific surface area. These may be zeolites of type X, Y or L containing at least 3% by weight of an alkali metal oxide (such as $Na_2O$), and preferably more than 10%. The sodium cation may also be replaced by another alkali metal cation.

The olefins to be used in the process according to the invention may be chosen from a very wide range. They contain at least one non-aromatic carbon-carbon double bond. They may generally be represented by the formula:

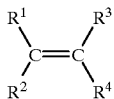

in which each of the symbols for $R^1$, $R^2$, $R^3$ and $R^4$, which are identical or different, represents a hydrogen atom, an aryl radical or an alkyl radical, linear, branched or cyclic, which contains from 1 to 20 carbon atoms and may contain one or more unsaturations and/or aromatic groups and/or $OR^5$, $SR^5$, $NR^5R^6$, CN, $COR^5$, $COOR^5$, $CONR^5R^6$, $SiR^5R^6R^7$, $Si(OR^5)R^6R^7$, $Si(OR^5)(OR^6)R^7$, $Si(OR^5)(OR^6)OR^7$, $SO_2R^5$, $SO_3R^5$, $POR^5R^6$, $OP(O)(OR^5)(OR^6)$, $NO_2$ or halogen groups, and each of the symbols for $R^5$, $R^6$ and $R^7$ denotes independently a hydrogen atom or an alkyl, cycloalkyl or aryl radical optionally containing one or more unsaturations.

Two of the symbols for $R^1$, $R^2$, $R^3$ and $R^4$ may also represent an unsubstituted or substituted alkylene group, that is to say that the carbon-carbon double bond may be included in a ring, for example in cyclohexene, cyclopentadiene, dicyclopentadiene, etc. The olefin of the invention may equally be an unsaturated or polyunsaturated fatty acid, an unsaturated or polyunsaturated fatty acid ester, a derivative of a fatty acid containing at least one double bond, or a mixture of the latter. For example, this compound may be oleic acid, linoleic acid, linolenic acid, palmitoleic acid or their esters of natural origin such as triglycerides or of synthetic origin such as, for example, esters of aliphatic alcohols or polyols. These fatty acids and esters may be used alone or mixed such as in natural fats, oils or fats of vegetable or animal origin, and derivatives thereof. Examples are sunflower oil, soybean oil, colza oil, rice bran oil, castor oil, tallow oil, tall oil, and the like. In the frame of the invention, the natural fats or their derivatives may contain some proportion of saturated acids or esters which act like solvents under the operating conditions of the invention.

The olefin of the invention may equally be a terpene, such as pinene, menthene, limonene, etc.

Mixtures of a number of olefins may also be used. By way of example, mention may be made of the mixture of a natural fat with an unfunctionallized aliphatic olefin.

It is preferable to use an olefin such as isobutylene, diisobutylene, triisobutylene, tripropylene, tetrapropylene, a fatty acid, a fatty ester, a mixture of fatty acids or esters, or an oil of vegetable or animal origin possibly mixed with an unfunctionallized aliphatic olefin.

The olefins used according to the invention may also be diluted in solvents. At the end of the reaction, these solvents are vented or separated by distillation. Examples of solvents of this type are saturated aliphatic hydrocarbons, such as methane, ethane, propane, a butane or a pentane. Using mixtures of this type made from olefins and saturated hydrocarbons can substantially improve the cost-effectiveness of the process according to the invention, in that starting materials of this type can be less costly than a relatively pure olefin-starting material. For example, it is possible to use a cut comprising saturated and unsaturated hydrocarbons having 4 carbon atoms in place of pure isobutylene.

The sulphur may be used in solid form, as pastilles, powder or in liquid form. The sulphur/olefin molar ratio may be from 0.4:1 to 2.5:1, preferably between 0.5:1 and 2:1.

The $H_2S$/olefin molar ratio may vary over a wide range (from 0.5:1 to 5:1 or even more), but it is preferable to use the minimum of $H_2S$ required for the reaction to work satisfactorily, or an $H_2S$/olefin ratio of between 0.5:1 and 2:1.

The process according to the invention may be worked batchwise or continuously.

The catalytic efficacy of the acid and basic catalysts can generally be seen from a minimum amount of 0.1% by weight of each of the two catalysts with respect to the amount of olefin. In most cases, the maximum useful amount is of the order of 30% by weight for each of the two catalysts. In a batch process the preferred amount is between 5 and 20% for each of the two catalysts.

When the process is worked continuously, one charge of catalyst may be used over long periods for preparing large amounts of product, and the catalyst/olefin ratio by weight is no longer of great significance.

The relative proportion of the two catalysts may vary widely. The acid catalyst/basic catalyst ratio by weight generally used is between 1:10 and 10:1, preferably between 1:2 and 2:1.

The process according to the invention may be worked in any appropriate equipment, for example in a reactor equipped with a stirrer, where the catalysts are in suspension in the liquid reaction medium. It may also be worked using a tubular reactor in which the catalysts are arranged in a fixed bed, in a moving bed or in an expanded bed; in this case, the acid catalysts and basic catalysts may be used mixed or in alternating layers.

The reaction itself may take place over a wide range of temperature, according to the olefins used and the type of catalysts employed. It is generally carried out at a temperature between 0 and 160° C., preferably between 0 and 110° C., more preferably between 20 and 90° C.

The reaction is conducted at a pressure appropriate to the conversion of the olefin. Operations are advantageously carried out at between 1 and 50 bar absolute, preferably between 1 and 20 bar absolute. The pressure may vary during the course of the reaction, particularly as a function of the temperature profile and of the progress of the reaction.

After a phase under pressure in a closed reactor where the olefin is converted, it is advantageous for the reactor head space to be set to atmospheric pressure or to subatmospheric pressure, so as to remove excess $H_2S$ and to complete conversion of the mercaptan formed. In this latter phase an inert gas may be introduced (for example methane, air or nitrogen) so as to entrain the residual volatiles, such as $H_2S$, or the residual olefin.

In the case of a batch reaction, at the end of the reaction the mixture of catalysts may be reclaimed by simple filtration and reutilized.

If it is desired to reduce the odor of the product, or to stabilise the same or reduce its corrosivity, the sulphurated product may be treated by any method known to the person skilled in the art. Methods of this type are described in the patents JP 58140063, U.S. Pat. Nos. 5,155,275, 5,206,439, 5,218,147, 5,403,961, 5,457,234, 5,530,163, 5,559,271, 5,091,112, 5,174,922, 5,208,382, 5,242,613, EP 76376 and EP 933 358 for example.

EXAMPLES

In the examples below, which illustrate the invention but do not limit the same, residual olefin in a reaction mixture was measured by gas chromatography, and mercaptan was measured by argentimetry. In Examples 1 to 7, the mercaptan measurement results have been related to a molecular weight of 202 (corresponding to that of the mercaptan derived from tetrapropylene).

Example 1

20 g of Amberlyst 15 acid resin (Röohm & Haas), which is a polystyrene-divinylbenzene macro-crosslinked resin having —$SO_3H$ functions with a specific surface area of about 50 $m^2/g$ and 1.8 mmol of sulphonic functions per ml of resin, and 25 g of DETA (polystyrene-divinylbenzene with diethylenetriamine functions) basic resin, the preparation of which is described in Example 1 of the patent EP 931 789, were introduced into a 1 liter stainless steel reactor inertized with nitrogen.

64 g of sulphur (2.0 mol) and 168 g of tetrapropylene (1.0 mol) were added, followed by, at 5° C., 27 g of hydrogen sulphide (0.8 mol), and the temperature was then brought to 90° C. with vigorous stirring.

The maximum pressure achieved was 7 bar absolute. After 3 hours, the reactor was connected to a flare, and once the pressure had been returned to 1.1 bar absolute, nitrogen-stripping took place for 3 hours.

A simple filtration on a metal grid situated at the base of the reactor gave a viscous, clear yellow-colored oil; the resins remain within the reactor.

The analyses (see Table 1) indicate that most of the tetrapropylene (shown as TP) has reacted and that the product comprises very little mercaptan.

Example 2

More sulphur, tetrapropylene and hydrogen sulphide were added to the charge of resins which served for Example 1, and a second operation was carried out under the above conditions. The results obtained were exactly the same as in Example 1.

Example 3

Example 1 was repeated, but using an initial TP/S/$H_2S$ molar ratio of 1/1.9/1.2.

The results indicated in Table 1 show that using a larger amount of $H_2S$ brings only a very slight improvement in the conversion of the tetrapropylene and increases the pressure in the reactor.

Example 4

Comparative

Example 3 was repeated, but without employing any catalyst.

The results are reported in Table 1. They show that, despite the elevated pressure achieved, there is no significant reaction of the tetrapropylene at the temperature of 90° C. Large amounts of solid sulphur are found to have remained in the reaction mixture.

Example 5

Comparative

Example 3 was repeated, but replacing the mixture of heterogeneous catalysts (A15+DETA) by the homogeneous catalyst n-butylamine.

Neither at 90° C. nor at 120° C. was any consumption of tetrapropylene detected. It is necessary to heat to above 130° C. (with a pressure of the order of 21–22 bar) before a significant conversion of tetrapropylene is detected after 3 hours.

Example 6

Comparative

Example 3 was repeated, but using DETA basic resin as sole catalyst. No significant reaction of the tetrapropylene was found (see Table 1). Large amounts of solid sulphur are found to have remained in the reaction mixture.

Example 7

Comparative

Example 3 was repeated, but using Amberlyst A15 acid resin as sole catalyst.

The resultant product comprises a very high proportion of residual tetrapropylene and of mercaptan.

Large amounts of solid sulphur are found to have remained in the reaction mixture.

TABLE 1

Reaction of tetrapropylene with sulphur and $H_2S$

| Ex. | Catalyst (s) | Ratio TP/S/$H_2S$ (mol) | Max. p. (bar absolute) | Temperature (° C.) | Residual TP % by weight | Mercaptan % by weight |
|---|---|---|---|---|---|---|
| 1 | A15 + DETA | 1/2/0.8 | 7 | 90° C. | 10% | 0.9% |
| 2 | A15 + DETA | 1/2/0.8 | 7 | 90° C. | 10% | 0.9% |
| 3 | A15 + DETA | 1/1.9/1.2 | 13 | 90° C. | 8% | 0.9% |
| 4* | None | 1/1.9/1.2 | 18 | 90° C. | >99% | <0.1% |
| 5* | n-$C_4H_9NH_2$ | 1/1.9/1.2 | 20 | 120° C. | >99% | <0.1% |
| 6* | DETA | 1/1.9/1.2 | 18 | 90° C. | >99% | <0.1% |
| 7* | A15 | 1/1.9/1.2 | 7 | 90° C. | 52% | 15% |

*Comparative examples

Example 8

In the reactor of Example 1, 30 g of Amberlyst A15 resin and 30 g of DETA resin were introduced, followed by 100 g of sulphur (3.1 mol) and 177 g of isoprene (2.6 mol). 72 g of $H_2S$ (2.1 mol) were added over 25 minutes at 20–25° C., and the temperature was then progressively increased to 40° C. (3 h) and then to 60° C. (4 h). The maximum pressure achieved was 12 bar absolute.

Analysis of a sample shows that the reaction mixture then comprised 0.7% of isoprene and 4.0% by weight of mercaptan (based on a molecular weight of 108).

After 2 hours of nitrogen-stripping at 60° C. at atmospheric pressure, no further isoprene was detected, and the proportion of mercaptan was 1.1%. Filtration on a metal grid at the base of the reactor gave 294 g of a clear yellow oil whose sulphur content is 48% by weight.

Example 9

In the reactor of Example 1, 30 g of Amberlyst A15 resin and 30 g of Amberlyst A21 basic resin (marketed by Röhm & Haas) were introduced, the latter being a macroporous polystyrene-divinylbenzene resin having —$CH_2N(CH_3)_2$ functions with a specific surface area of about 25 $m^2/g$ and 1.3 mmol of tertiary amine functions per ml of resin. 154 g of sulphur (4.8 mol) and 336 g of diisobutylene (3.0 mol) were then added. 84 g of $H_2S$ (2.5 mol) were then added over 60 minutes at 30° C. The temperature was brought to 60° C. and the mixture allowed to react for 3 hours. The maximum pressure achieved was 9 bar absolute.

Analysis of a sample shows that the reaction mixture at this stage comprised 2% of diisobutylene and 3.4% by weight of mercaptan (based on a molecular weight of 146).

After 2 hours of nitrogen-stripping at 60° C. at atmospheric pressure, the diisobutylene content was 2% and the mercaptan content was 0.7%. Filtration on a metal grid at the base of the reactor gave 558 g of a clear yellow oil whose sulphur content is 36.7% by weight.

Example 10

In the reactor of Example 1, 30 g of Amberlyst A15 resin and 30 g of LZY-52 zeolite extrudates (marketed by UOP), a type Y exchanged zeolite typically comprising 10.4% of sodium oxide, 0.3% of calcium oxide, 0.2% of ironIII oxide, 66.5% of silica and 20.8% of alumina, and having a specific surface area of about 820 m$^2$/g, were introduced. 153 g of sulphur (4.8 mol) and 336 g of diisobutylene (3.0 mol) were then introduced. 82 g of H$_2$S (2.4 mol) were then added over 50 minutes at 20–30° C. The temperature was brought to 88° C. and the mixture allowed to react for 4 hours. The maximum pressure achieved was 12 bar absolute.

Analysis of a sample shows that the reaction mixture at this stage comprised 3.0% of diisobutylene and 3.9% by weight of mercaptan (based on a molecular weight of 146).

After 2 hours of nitrogen-stripping at 60° C. at atmospheric pressure, the diisobutylene content was 4% and the mercaptan content 1.5%. Filtration on a metal grid at the base of the reactor gave a clear yellow oil.

Example 11

In the reactor of Example 1, 18 g of Amberlyst A15 resin and 18 g of DETA resin were introduced, followed by 60 g of sulphur (1.9 mol) and 122 g of isobutylene (2.2 mol). 69 g of H$_2$S (2.0 mol) were added over 70 minutes at 30° C., and the mixture was allowed to react at this temperature for 3 hours. The maximum pressure achieved was 5.5 bar absolute.

Analysis of a liquid sample shows that the reaction mixture at this stage comprised 0.2% of isobutylene and 32% by weight of tert-butyl mercaptan (expressed as percentage of air on the chromatogram).

The pressure on the reactor contents was then reduced. Analysis of the gas discharged in this reduction of pressure showed an isobutylene content of 0.6% by weight. The liquid phase in the reactor comprised 0.15% by weight of isobutylene. The total conversion of isobutylene is about 99%.

2 hours of nitrogen-stripping at 60° C. gave a product with an isobutylene content of 0.1% and a mercaptan content (based on a molecular weight of 92) of 1.1%.

Filtration on a metal grid at the base of the reactor gave a crude product with the appearance of a clear yellow oil.

Example 12

In the reactor of Example 1, 30 g of Amberlyst A15 resin and 30 g of DETA resin were introduced, followed by 77 g of sulphur (2.4 mol) and 196 g of mesityl oxide (2.0 mol). 54 g of H$_2$S (1.6 mol) were added over 30 minutes at 30° C., and the mixture was allowed to react at this temperature for 2 hours, then at 60° C. for 2 hours. The maximum pressure achieved was 5.5 bar absolute.

Analysis of a liquid sample shows that the reaction mixture now comprises no detectable amount of mesityl oxide. The mercaptan content (based on a molecular weight of 130) was 6.3%.

The pressure on the reactor contents was reduced. 4 hours of nitrogen-stripping at 70° C. gave a product with a mercaptan content of 0.6% by weight (based on a molecular weight of 130).

Filtration on a metal grid at the base of the reactor gave a crude product with the appearance of a clear yellow oil.

Example 13

In the reactor of Example 1, 30 g of Amberlyst A15 resin and 30 g of DETA resin were introduced, followed by 46 g of sulphur (1.4 mol) and 202 g of n-dodecene (1.2 mol). 33 g of H$_2$S (1.0 mol) were added over 25 minutes at 25° C., and the mixture was allowed to react at 65° C. for 3 hours, then at 80° C. for 3 hours. The maximum pressure achieved was 8 bar absolute.

The pressure on the reactor contents was reduced. 3 hours of nitrogen-stripping at 80° C. gave a product with a mercaptan content of 1.5% by weight (based on a molecular weight of 202) and its n-dodecene content was 8.5% by weight.

Filtration on a metal grid at the base of the reactor gave a crude product with the appearance of a clear yellow oil.

Example 14

In the reactor of Example 1, 30 g of Amberlyst A15 resin and 30 g of DETA resin were introduced, followed by 38 g of sulphur (1.2 mol) and 268 g of oleic alcohol (1.0 mol). 27 g of H$_2$S (0.8 mol) were added over 15 minutes at 25° C. and the mixture was allowed to react at 70° C. for 4 hours. The maximum pressure achieved was 9 bar absolute.

The pressure on the reactor contents was reduced. 4 hours of nitrogen-stripping at 60° C. gave a product with a mercaptan content of 1.8% by weight (based on a molecular weight of 202) and its oleic alcohol content was 5.1% by weight.

Filtration on a metal grid at the base of the reactor gave a crude product with the appearance of a clear yellow oil.

Example 15

In the reactor of example 1, 30 g of Amberlyst 15 and 30 g of extrudates of LZY-54 zeolite (marketed by UOP), an exchanged zeolite of Y type typically containing 10% of sodium oxide, 0.23% of iron III oxide, 66% of silica and 21% of alumina, and having a specific surface area of about 750 m$^2$/g, were introduced. 28.4 g of sulphur (0.89 mol) and 250 g of technical methyl oleate marketed by FINA CHEMICALS and containing 55% of methyl oleate (that is 0,46 mol) were then introduced. The temperature was brought to 126° C. and hydrogen sulphide was continuously added in order to keep a pressure of 13 bar absolute in the reactor. After 9 hours in those conditions, total uptake of hydrogen sulphide was 33 g.

After 1 hour nitrogen-stripping at atmospheric pressure, the reaction mixture contained 4.6% methyl oleate. Filtration gave 255 g of a yellow-orange oil. No solid sulphur deposit was found either in the liquid phase or on the filter.

Example 16

In the reactor of example 1, 30 g of Amberlyst 15 and 30 g of LZY-54 zeolite were introduced. 28.4 g of sulphur (0.89 mol) and 250 g of a mixture of methyl esters, marketed by FINA CHEMICALS and coming from methyl ricinoleate cracking, which contained 29% of methyl linoleate (0.24 mol), 50% of methyl oleate (0.42 mol) and some methyl stearate and methyl palmitate were then introduced. The temperature was brought to 126° C. and hydrogen sulphide was continuously added in order to keep a pressure of 9 bar absolute in the reactor. After 12 hours under those conditions, total uptake of hydrogen sulphide was 27 g.

After 2 hours nitrogen-stripping at atmospheric pressure and at 80° C., the reaction mixture contained 3.2% methyl oleate and methyl linoleate was not detected anymore. Filtration gave 261 g of a yellow-orange oil. No solid sulphur deposit was found either in the liquid phase or on the filter.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. Process for manufacturing sulphurized olefins from olefin(s), sulphur and hydrogen sulphide, comprising carrying out in one step a reaction in the presence of a solid acid catalyst and of a solid basic catalyst.

2. Process according to claim 1, wherein the solid acid catalyst is a cation-exchange resin, a zeolite of acid character, a silica-alumina, a sulphated zirconia, a supported heteropolyanion, or a mixture of these solids.

3. Process according to claim 1, wherein the solid acid catalyst is a cation-exchange resin.

4. Process according to claim 1, wherein the solid basic catalyst is an anion-exchange resin, a zeolite of basic character, an alumina or silica-alumina doped with alkali metals or with alkaline earth metals, or a mixture of these catalysts.

5. Process according to claim 1, wherein the solid basic catalyst is an anion-exchange resin.

6. Process according to claim 1, wherein the sulphur/olefin(s) molar ratio is from 0.4:1 to 2.5:1.

7. Process according to claim 1, wherein the $H_2S$/olefin(s) molar ratio is from 0.5:1 to 5:1.

8. Process according to claim 1, wherein each of the two catalysts is used in an amount of from 0.1 to 30% by weight with respect to the weight of olefin(s).

9. Process according to claim 1, wherein the acid catalyst/basic catalyst ratio by weight is between 1:10 and 10:1.

10. Process according to claim 1, wherein operations are carried out at a temperature of from 0 to 160° C.

11. Process according to claim 1, wherein operations are carried out at a pressure of from 1 to 50 bar absolute.

12. Process according to claim 1, wherein the olefin(s) are selected from those of formula:

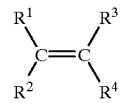

in which each of the symbols for $R^1$, $R^2$, $R^3$ and $R^4$, which are identical or different, represents a hydrogen atom, an aryl radical or an alkyl radical, linear, branched or cyclic, which contains from 1 to 20 carbon atoms and optionally contain at least one unsaturation and/or aromatic group and/or $OR^5$, $SR^5$, $NR^5R^6$, CN, $COR^5$, $COOR^5$, $CONR^5R^6$, $SiR^5R^6R^7$, $Si(OR^5)R^6R^7$, $Si(OR^5)(OR^6)R^7$, $Si(OR^5)(OR^6)OR^7$, $SO_2R^5$, $SO_3R^5$, $POR^5R^6$, $OP(O)(OR^5)(OR^6)$, $NO_2$ or halogen group, each of the symbols for $R^5$, $R^6$ and $R^7$ denoting independently a hydrogen atom or an alkyl, cycloalkyl or aryl radical optionally containing at least one unsaturation, and two of the symbols for $R^1$, $R^2$, $R^3$ and $R^4$ optionally also represent an unsubstituted or substituted alkylene group.

13. Process according to claim 12, wherein the olefin(s) is selected from the group consisting of isobutylene, diisobutylene, triisobutylene, tripropylene or tetrapropylene.

14. Process according to claim 12, wherein the olefin(s) is selected from the group consisting of a fatty acid, a fatty ester, a mixture of fatty acids or esters, or an oil of animal or vegetable origin.

15. Process according to claim 12, wherein the olfein(s) is selected from the group consisting of a mixture of an unfunctionalized aliphatic olefin with a fatty acid, a fatty ester or an oil of animal or vegetable origin.

16. Process according to claim 3, wherein the catalyst is a sulphonated resin based on a polystyrene crosslinked with divinylbenzene.

17. Process according to claim 5, wherein the catalyst is a resin based on polystyrene crosslinked with divinylbenzene and bearing amine, quaternary ammonium, polyethylene polyamine, guanidine or amidine functional groups.

18. Process according to claim 6, wherein the molar ratio is between 0.5:1 and 2:1.

19. Process according to claim 7, wherein the molar ratio is between 0.5:1 and 2:1.

20. Process according to claim 8, wherein the amount of catalyst is between 5 and 20%.

21. Process according to claim 9, wherein the ratio is between 1:2 and 2:1.

22. Process according to claim 10, wherein the temperature is between 0 and 100° C.

23. Process according to claim 10, wherein the temperature is between 20 and 90° C.

24. Process according to claim 11, wherein the temperature is between 1 and 20 bar absolute.

* * * * *